United States Patent [19]

Kwantes et al.

[11] 4,191,843

[45] Mar. 4, 1980

[54] PREPARATION OF BISPHENOLS

[75] Inventors: Ariën Kwantes; Pieter A. Gautier, both of Amsterdam, Netherlands

[73] Assignee: Shell Oil Company, Houston, Tex.

[21] Appl. No.: 958,576

[22] Filed: Nov. 7, 1978

[30] Foreign Application Priority Data

Nov. 9, 1977 [GB] United Kingdom ............... 46644/77

[51] Int. Cl.$^2$ ...................... C07C 37/20; C07C 39/16; C07C 37/00
[52] U.S. Cl. ..................................... 568/728; 568/723; 568/724; 568/725; 568/726; 568/727; 568/730
[58] Field of Search ............... 568/717, 718, 719, 720, 568/721, 722, 723, 724, 725, 726, 727, 728, 730

[56] References Cited

U.S. PATENT DOCUMENTS

| | | | |
|---|---|---|---|
| 2,730,552 | 1/1956 | Williamson | 568/728 |
| 3,049,568 | 8/1962 | Apet et al. | 568/728 |
| 3,169,996 | 2/1965 | Bostran et al. | 568/728 |
| 3,221,061 | 11/1965 | Grover et al. | 568/728 |
| 4,045,379 | 8/1977 | Kwantes et al. | 568/728 |

FOREIGN PATENT DOCUMENTS

| | | |
|---|---|---|
| 849965 | 9/1960 | United Kingdom . |
| 937072 | 9/1963 | United Kingdom . |
| 1183564 | 3/1970 | United Kingdom . |
| 1272585 | 5/1972 | United Kingdom . |
| 1361430 | 7/1974 | United Kingdom . |

*Primary Examiner*—Norman Morgenstern

[57] ABSTRACT

A process for the preparation of bisphenols is described which comprises reacting, in a reaction zone, at least 2 moles of a phenol with a carbonyl compound, at a temperature of from 40° to 95° C., in the presence of an acid ion exchanger, optionally partially modified with a compound having an acidic reacting group and a mercaptan group, and recovering the bisphenols from the reaction zone effluent, characterized in that the reaction zone effluent is contacted with an acid ion exchanger in metal salt form and/or a weak base ion exchanger. As a result, it has been found that the formation of undesirable compounds is substantially reduced.

5 Claims, No Drawings

PREPARATION OF BISPHENOLS

BACKGROUND OF THE INVENTION

It is known to prepare bisphenols, e.g., diphenylolpropanes, by reacting, in a reaction zone, at least 2 moles of a phenol, e.g., phenol itself, with a carbonyl compound, e.g., acetone, at a temperature of from 40° to 95° C., in the presence of an acid exchanger, e.g., a sulphonated ion-exchange resin, e.g., see British Pat. No. 849,965.

The reaction zone effluent may be worked-up in a various ways to recover the bisphenols therefrom. For example, substantially all of the unreacted carbonyl compound and water may be removed from the reaction zone effluent and the bisphenols recovered from the remainder of the reaction zone effluent.

One disadvantage of the known process is that undesirable compounds are formed during the working-up which contaminate the recovered bisphenols. It is not possible to identify positively these undesirable compounds but their presence may be detected by high performance liquid chromatography as hereinafter described.

It has now been found that the formation of these undesirable compounds is substantially reduced if the reaction zone effluent is contacted with an acid ion exchanger in metal salt form and/or a weak base ion exchanger.

SUMMARY OF THE INVENTION

The present invention is concerned with a process for the preparation of bisphenols comprising reacting, in a reaction zone, at least 2 moles of a phenol with a carbonyl compound, at a temperature of from 40° to 95° C., in the presence of an acid ion exchanger, optionally partially modified with a compound having an acidic reacting group and a mercaptan group, and recovering the bisphenols from the reaction zone effluent, characterized in that the reaction zone effluent is contacted with an acid ion exchanger in metal salt form and/or a weak base ion exchanger.

After the reaction zone effluent has been contacted with the acid ion exchanger in metal salt form and/or the weak base ion exchanger, substantially all of the unreacted carbonyl compound and water are separated therefrom and the bisphenols recovered from the residue of the separation. This may suitably be achieved by separating, e.g., by distillation, the contacted reaction zone effluent into two streams, the first stream comprising unreacted carbonyl compound, water and phenol and the second stream comprising bisphenols, reaction by-products and phenol. The separation may take place in two or more stages. The contacted reaction zone effluent, depending on the temperature thereof and the pressure used, may be heated or cooled to effect this separation. In the case of a distillation column, the temperature thereof is suitably maintained at a bottom temperature of from 130° to 220° C. and a top temperature of from 20° to 100° C., and the pressure thereof should be sufficient to completely separate the carbonyl compound and water and a part of the phenol from the reactor zone effluent. In practice the amount of phenol removed is the minimum amount removed during the complete removal of the unreacted carbonyl compound and water. The stream thus obtained, which preferably amounts to from 1 and 10%w of the reaction zone effluent, may be worked-up and the unreacted carbonyl compound and phenol recycled.

The residue of the separation, i.e., the second stream, comprises bisphenols, reaction by-products and phenol. Suitably the amount of phenol is this stream is from 4 to 15 moles per mole of bisphenols. The bisphenols may be recovered from the second stream by conventional techniques, such as by the removal of the phenol therefrom by evaporation. The bisphenols may also be recovered by crystallization and separation of the bisphenols in the form of adducts thereof with the phenol, followed by evaporation of the phenol from the adducts.

DESCRIPTION OF THE PREFERRED EMBODIMENT

According to a preferred aspect of the present invention the acid ion exchanger used in the reaction zone is a partially modified ion exchanger of the type described herein and according to this preferred aspect the reaction zone effluent is preferably first contacted with an acid ion exchanger before it is contacted with the acid ion exchanger in metal salt form and/or the weak base ion exchanger.

The reaction zone may comprise a single reactor or two or more reactors in series. In the case of a multireactor reaction zone, suitably all of the phenol is fed to the first reactor and the carbonyl compound is either fed all to the first reactor or divided between the first and second and possibly further reactors.

The acid ion exchangers for use in the reaction zone are suitably strong-acid ion exchangers, such as those resins or polymers having a plurality of pendant sulphonic acid groups. Examples include sulphonated polystyrene or poly(styrene-divinylbenzene) copolymers and sulphonated phenol-formaldehyde resins. The sulphonated resins are commercially available in a dry or water swollen form and either form may be used in the process. Specific examples of suitable resins are Amberlite IR-120H, Amberlyst 15H, Dowex 50-X-4, Dowex MSC-1H, Duolite c-26, Permutit QH, Chempro C-20 and Imac C8P/H (Amberlite, Amberlyst, Dowex, Duolite, Permutit, Chempro and Imac are registered Trade Marks). Further examples of such ion exchangers as well as methods for preparing such ion exchangers are described in the Encyclopedia of Polymer Science and Technology, 1967, vol. 7, pages 695 to 708. The exchange capacity of the acidic resin is preferably at least 2.0 meq. $H^+/g$ of dry resin, with exchange capacities in the range of from 3.0 to 5.5 meq. $H^+/g$ dry resin being particularly preferred.

The reactor may be filled with the acid ion exchanger by any known technique. Such techniques include adding the desired amount of dry ion exchanger, water-wet ion exchanger or slurry of the ion exchanger to the reactor. The catalyst bed is suitably fixed and is usually supported on one or more grids.

Suitable phenols for use in the present invention should have a reactive hydrogen atom, preferably in the para-position relative to the phenolic hydroxyl group. Such phenols may be substituted by one or more alkyl groups, e.g., lower alkyl groups, such as methyl or tertiary butyl groups; halogen atoms, such as chlorine atoms, or other non-interfering substituents. Specific examples of phenols include ortho- and meta-cresol; 2,6-dimethylphenol; ortho-sec. butylphenol; ortho-tert. butylphenol; 2,6-di-tert.butylphenol; 1,3,5-xylenol; tetramethylphenol; 2-methyl-6-tert. butylphenol; ortho-phenylphenol; ortho- and meta-chlorophenol; orthobromphenol; 6-chloro-ortho-cresol and 2,6-dichlorophenol. Phenol itself is the preferred phenol.

The carbonyl compounds used in the process may be aldehydes or ketones with the latter being preferred. Preferred ketones are those having at least one methyl group in the alpha-position relative to the carbonyl group or are cyclic ketones. Specific examples include acetone, methyl ethyl ketone, methyl propyl ketone, acetophenone, methyl vinyl ketone and cyclohexanone. Acetone is the preferred ketone. The present invention is particularly suitable for the preparation of 2,2-bis(4-hydroxyphenyl)propane (Bisphenol A).

The molar ratio of phenol to carbonyl compound is at least 2 with a stoichiometric excess of phenol being preferred. Suitable molar ratios are from 3:1 to 40:1, with molar ratios of from 10:1 to 30:1 being preferred. The optimum ratio depends inter alia on reaction conditions, e.g., temperature of reaction and desired conversion.

The reaction temperature in the reactor zone may, as described above, vary from 40° C. to 95° C. with reaction temperatures in the range of from 55° to 90° C. being preferred.

The reaction time in the reactor zone may also vary between limits and depends inter alia on reaction temperature. For example, the liquid hour space velocity (LHSV) of the feed may vary between wide limits with velocities in the range of from 0.2 to 40 liters feedstream.liter catalyst$^{-1}$.hour$^{-1}$ being suitable.

The acid ion exchangers in metal salt form for use in the present invention are suitably strong-acid ion exchangers in metal salt form, such as those resins or polymers having a plurality of pendant metal sulphonate groups. Examples of acid ion exchangers include those described above. Suitably such acid ion exchangers are in the alkali-metal, e.g., sodium and/or potassium, form. Substantially all of the acid groups are in metal salt form.

The weak base ion exchangers for use in the present invention are suitably those resins or polymers having a plurality of pendant primary and/or secondary and/or tertiary amino groups. Some pendant quarternary amino groups may also be present. Examples include amino derivatives of chloromethylated polystyrene or poly(styrene-divinylbenzene); condensation products of epichlorohydrin with amines or ammonia and aminated products of phenol and formaldehyde. Methods of preparing such resins or polymers, as well as some commercially available forms thereof, are described in the Encyclopedia of Polymer Science and Technology, vol. 7, 1967, pages 695 to 708. It is necessary that the ion exchanger should be stable at the temperature at which the reaction zone effluent is contacted with it and for this reason ion exchangers based on polystyrene or poly(styrenedivinylbenzene) are preferred.

The amount of acid ion exchanger in metal salt form and/or weak base ion exchanger with which the reaction zone effluent is contacted is not critical and may vary from 10 to 100%v, e.g., the reaction zone.

As stated hereinbefore the acid ion-exchange resin may be partially modified. The acid ion exchanger may be partially modified with a compound having an acidic reacting roups and a mercaptan group. Modification may be carried out by either partially esterifying the resin with a mercapto alcohol (e.g., see U.K. Pat. No. 937,072) or by partially neutralizing the resin with an alkyl mercapto-amine, such as thioethanolamine (e.g., see Belgian Pat. No. 589,727 and U.K. Pat. No. 1,183,564), precursors of alkyl mercapto-amines, such as thiazolidines (e.g., see U.K. Pat. No. 1,361,430), cyclomercaptoamines and mercaptoaminocarboxylic acid, as well as thiazolidine precursors of the latter as described in Netherlands published Specification No. 7608352. Suitably from 2 to 25%, preferably from 5 to 20%, of the acidic groups are modified. Such modified acid ion exchangers may be prepared by using the techniques described in the above references or by the technique described in Netherlands published Specification No. 7608352 or by using a draft tube reactor of the type described in U.K. Pat. No. 1,272,585. As an alternative to such modification, the reaction may be carried out in the presence of a dissolved sulphur compound as promoter; examples include alkyl mercaptans, such as methyl and ethyl mercaptan and mercapto-substituted aliphatic carboxylic acids, such as 3-mercapto propionic acid.

When such a modified ion exchanger is used in the reaction zone it is desirable that the reaction zone effluent is contacted with an acid ion exchanger of the type described above before it is contacted with the acid ion exchanger in metal salt form and/or the weak-base ion exchanger. Sulphonated ion exchangers are particularly suitable for this purpose. The amount of acid ion exchanger with which the reaction zone effluent is contacted is not critical and may vary from 10 to 100%v, e.g., from 15 to 50%v of the volume of the acid ion exchanger used in the reaction zone.

It may be desirable to wash and/or regenerate the ion exchangers periodically. Suitably, the ion exchangers may be washed with mixtures of water and solvents, for the impurities, such as alcohols, e.g., methanol or phenols, e.g., phenol itself.

The bisphenols so prepared may be used in a variety of applications, such as to prepare anti-oxidants, epoxy resins and polycarbonate resins.

The invention will be illustrated with reference to the following examples. It will be appreciated that the following examples are for the purpose of illustration only and is no way intended to limit the invention to the particular compositions or process conditions. Modifications within the spirit and scope of the present invention will become apparent to those skilled in the art.

Parts and percentages therein are parts by weight and percentages by weight, unless stated otherwise.

The term "DPP" means diphenylol propane or bisphenol.

EXAMPLE 1 (comparative)

A tubular reactor (150 cm long; 2 cm internal diameter), connected in series with a distillation column (150 cm long; 2 cm internal diameter), was partially filled with an aqueous slurry containing 175 g (dry basis) of a partially modified sulphonated styrene/divinylbenzene acidic ion exchange resin having an exchange capacity of 5.00 meq. H$^+$/g dry resin, and the water drained off to form a fixed bed of resin. The partially modified resin had been prepared by neutralizing 13% of the acidic groups of the resin with thioethanolamine. The reactor was maintained at a temperature of 65° C. and the distillation column was maintained at a bottom temperature of 194° C.

A feedstream comprising phenol and acetone (molar ratio 15:1) was continuously passed through the reactor at a liquid hour space velocity of 5 liters.liter catalyst$^{-1}$.hour$^{-2}$ and the reaction zone effluent continuously withdrawn and fed to the distillation column from which a top stream (distillate stream) and a bottom stream (recovery stream) were continuously withdrawn. The top stream consisted of all of the acetone and water which were present in the reactor effluent and contained 8%w phenol and the recovery stream consisted of the remainder of the reaction zone effluent.

The reaction zone effluent and the recovery stream were analyzed by high performance liquid chromatography using a column filled with microBondapak $C_{18}$ Methanolic solutions (10 microliters) of the products to be analyzed (1.5 g in 50 ml of methanol) were passed into the column and the column eluted separately with 50/50 w/w methanol/water and 60/40 w/w methanol/water. The compounds in the elutions were detected by U.V. adsorption at 254 nm. The peak obtained (50/50 w/w methanol/water) just ahead of the main p,p-DPP peak is described as the alpha-compound and the main p,p-DPP peak is described as the alpha-compound and the peaks obtained (60/40 w/w methanol/water) after the main o,o-DPP peak but before the BPX peak are described as beta- and gamma-compounds. The results for the recovery stream are presented in Table I. The results for the reactor zone effluent are the same as for the recovery stream except that substantially no alpha-, beta- or gamma-compounds were detected therein.

TABLE I

| Run hours | Acetone conversion (% m) | Yield of DPP (% w on recovery stream | o,p/p,p ratio (w) | alpha-, beta-, gamma-compounds surface area/surface area of p,p-DPP (DPP = 100) |
|---|---|---|---|---|
| 25 | 58 | 9.2 | 2.5/97.5 | 5.0 |
| 50 | 56 | 8.9 | 2.4/97.5 | 4.8 |
| 100 | 54 | 8.6 | 2.5/97.5 | 4.7 |
| 200 | 50 | 8.0 | 2.4/97.6 | 4.7 |
| 400 | 46 | 7.3 | 2.5/97.5 | 4.6 |

*all material boiling above the boiling point of phenol.

EXAMPLE 2

Example 1 was repeated with the difference that the reaction zone effluent, before being fed to the distillation column, was passed through a column (40 cm long; 2 cm internal diameter) partially filled with 48 g (dry basis) of a sulphonated styrene/divinyl benzene ion-exchange resin in the sodium form having an exchange capacity of 5.00 meq. Na$^+$/g dry resin.

The results are presented in Table II.

TABLE 2

| Run hours | Acetone conversion (% m) | Yield of DPP* (% w on recovery stream) | o,p/p,p ratio (w) | alpha-, beta-, gamma-compounds area/surface area of p,p-DPP (DPP = 100) |
|---|---|---|---|---|
| 25 | 58 | 9.2 | 2.6/97.4 | 1.2 |
| 50 | 56 | 8.9 | 2.5/97.5 | 1.0 |
| 100 | 54 | 8.6 | 2.4/97.6 | 0.9 |
| 200 | 50 | 8.0 | 2.4/97.6 | 0.9 |
| 400 | 46 | 7.3 | 2.5/97.5 | 0.9 |

*all material boiling above the boiling point of phenol.

EXAMPLE 3

Example 2 was repeated with the difference that the reaction zone effluent, before being passed through a column partially filled with 30 g of the sulphonated styrene/divinylbenzene ion exchange resin in the sodium form, was first passed through a column (25 cm long; 2 cm internal diameter) partially filled with 30 g (dry basis) of a sulphonated styrene/divinyl benzene acidic ion exchange resin having an exchange capacity of 5.00 meq. H$^+$/g dry resin.

The results are presented in Table III.

TABLE III

| Run hours | Acetone conversion (% m) | Yield of DPP (% w on recovery stream) | o,p/p,p ratio (w) | alpha-, beta-, gamma-compounds surface area/surface area of p,p-DPP (DPP = 100) |
|---|---|---|---|---|
| 25 | 59 | 9.4 | 2.5/97.5 | 0.05 |
| 50 | 58 | 9.2 | 2.6/97.4 | 0.05 |
| 100 | 56 | 8.9 | 2.5/97.5 | 0.05 |
| 200 | 52 | 8.3 | 2.5/97.5 | 0.05 |
| 400 | 48 | 7.7 | 2.4/97.6 | 0.05 |

*all material boiling above the boiling point of phenol.

EXAMPLE 4

Example 3 was repeated with the difference that the column of sulphonated styrene/divinylbenzene ion-exchange resin in the sodium form was replaced by a column (40 cm long; 2 cm internal diameter) partially filled with 35 g (dry basis) of an ion-exchange resin having free primary and secondary amino groups attached thereto and having an exchange capacity of 3.5 meq./dry resin.

The results are presented in Table IV.

TABLE IV

| Run hours | Acetone conversion (% m) | Yield of DPP* (% w on recovery stream) | o,p/p,p ratio (w) | alpha-, beta-, gamma-compounds surface area/surface area of p,p-DPP (DPP = 100) |
|---|---|---|---|---|
| 25 | 58 | 9.2 | 2.5/97.5 | 0.3 |
| 50 | 56 | 8.9 | 2.4/97.6 | 0.2 |
| 100 | 54 | 8.6 | 2.5/97.5 | 0.2 |
| 200 | 50 | 8.0 | 2.6/97.4 | 0.2 |
| 400 | 46 | 7.3 | 2.5/97.5 | 0.2 |

*all material boiling above the boiling point of phenol.

What is claimed is:

1. In a process for the preparation of bisphenols comprising reacting, in a reaction zone, at least 2 moles of a phenol with a carbonyl compound, at a temperature of from 40° to 95° C., in the presence of an acid ion exchanger, optionally partially modified with a compound having an acidic reacting group and a mercaptan group, and recovering the bisphenols from the reaction zone effluent, the improvement which comprises contacting the reaction zone effluent with an acid ion exchanger in metal salt form and/or a weak base ion exchanger.

2. The process of claim 1, wherein the acid ion exchanger in metal salt form is an ion exchanger having a plurality of pendant alkali-metal sulphonate groups.

3. The process of claim 1, wherein the weak base ion exchanger is an ion exchanger having a plurality of pendant primary and/or secondary and/or tertiary amino groups.

4. The process of claim 1, wherein after the reaction zone effluent has been contacted with the acid ion exchanger in metal salt form and/or the weak base ion exchanger, substantially all of the unreacted carbonyl compound and water are separated therefrom and the bisphenols recovered from the residue of the separation.

5. The process of claim 2, wherein the acid ion exchanger used in the reaction zone is an acid ion exchanger partially modified with a compound having an acidic reacting group and a mercaptan group, and that the reaction zone effluent is contacted with an acid exchanger before it is contacted with the acid ion exchanger in metal salt form and/or the weak base ion exchanger.

* * * * *